(12) United States Patent
Kuramochi

(10) Patent No.: US 9,869,702 B2
(45) Date of Patent: Jan. 16, 2018

(54) CURRENT MEASUREMENT CIRCUIT

(71) Applicant: ADVANTEST CORPORATION, Nerima-ku, Tokyo (JP)

(72) Inventor: Yasuhide Kuramochi, Tokyo (JP)

(73) Assignee: ADVANTEST CORPORATION, Tokyo (JP)

( * ) Notice: Subject to any disclaimer, the term of this patent is extended or adjusted under 35 U.S.C. 154(b) by 177 days.

(21) Appl. No.: 14/925,017

(22) Filed: Oct. 28, 2015

(65) Prior Publication Data

US 2016/0154032 A1    Jun. 2, 2016

(30) Foreign Application Priority Data

Nov. 28, 2014  (JP) .................................. 2014-242019

(51) Int. Cl.
*G01R 19/00*   (2006.01)
*H03F 3/45*    (2006.01)
(Continued)

(52) U.S. Cl.
CPC ....... *G01R 19/0023* (2013.01); *C12Q 1/6869* (2013.01); *G01N 33/48721* (2013.01);
(Continued)

(58) Field of Classification Search
None
See application file for complete search history.

(56) References Cited

U.S. PATENT DOCUMENTS

| 6,433,552 B1 * | 8/2002 | Williams | G01R 29/24 |
| | | | 324/455 |
| 8,628,649 B2 * | 1/2014 | Lindsay | B82Y 15/00 |
| | | | 204/403.01 |

(Continued)

FOREIGN PATENT DOCUMENTS

| JP | H07131255 A | 5/1995 |
| JP | H11101807 A | 4/1999 |

(Continued)

*Primary Examiner* — Paresh Patel
(74) *Attorney, Agent, or Firm* — Cantor Colburn LLP

(57) ABSTRACT

A current measurement circuit converts a current signal $I_{IN}$ into a voltage signal $V_{OUT}$. The current signal $I_{IN}$ is transmitted via a signal line. A shield line is arranged in the vicinity of at least a part of the signal line. A non-inverting amplifier includes an operational amplifier, and the current signal $I_{IN}$ is input to its non-inverting input terminal. The output signal of the non-inverting amplifier is input to its inverting input terminal as a feedback signal. An inverting amplifier amplifies the output signal of the non-inverting amplifier with inversion so as to generate a voltage signal $V_{OUT}$. An impedance circuit includes a feedback resistor $R_F$ between the output terminal of the inverting amplifier and the non-inverting input terminal of the operational amplifier. A guard amplifier receives the electric potential at the inverting input terminal of the operational amplifier, and applies the electric potential to the shield line.

9 Claims, 12 Drawing Sheets

(51) Int. Cl.
  *G05F 1/56* (2006.01)
  *G01N 33/487* (2006.01)
  *C12Q 1/68* (2006.01)
  *B82Y 15/00* (2011.01)
  *H03F 1/34* (2006.01)

(52) U.S. Cl.
  CPC ......... *G05F 1/561* (2013.01); *H03F 3/45475* (2013.01); *B82Y 15/00* (2013.01); *G01R 19/0092* (2013.01); *H03F 1/34* (2013.01); *H03F 2200/261* (2013.01); *H03F 2200/462* (2013.01); *H03F 2203/45138* (2013.01); *H03F 2203/45156* (2013.01)

(56) References Cited

U.S. PATENT DOCUMENTS

| | | | | |
|---|---|---|---|---|
| 8,961,757 B2 * | 2/2015 | Nuckolls | ............ | C12Q 1/6869 |
| | | | | 204/403.01 |
| 2008/0100300 A1 * | 5/2008 | Williams | ........... | G01R 19/0023 |
| | | | | 324/458 |
| 2009/0167324 A1 * | 7/2009 | Prance | ................. | G01R 15/165 |
| | | | | 324/658 |
| 2013/0300435 A1 * | 11/2013 | Chi | .................... | G01R 19/0023 |
| | | | | 324/658 |

FOREIGN PATENT DOCUMENTS

| | | |
|---|---|---|
| JP | 2004012330 A | 1/2004 |
| JP | 2013066176 A | 4/2013 |

\* cited by examiner

CURRENT MEASUREMENT CIRCUIT

CROSS-REFERENCE TO RELATED APPLICATIONS

The present invention claims priority under 35 U.S.C. §119 to Japanese Application No. 2014-242019, filed Nov. 28, 2014, the entire content of which is incorporated herein by reference.

BACKGROUND OF THE INVENTION

Field of the Invention

The present invention relates to a current measurement circuit.

Description of the Related Art

In order to analyze the base sequence of DNA (deoxyribonucleic acid), RNA (ribonucleic acid), or the like, a base sequence analyzing apparatus (sequencer) is employed. As a next-generation (fourth-generation) sequencer, various kinds of techniques have been sought by research institutions and industries. As one of such prospective techniques, the gating nanopore sequencing technique has attracted attention.

With the gating nanopore sequencing technique, DNA or RNA is moved such that it passes through a gap between a pair of nanometer-order electrodes (nano-electrodes). The tunnel current that flows through the electrode gap changes according to the base type (A, G, T, C) that passes through the electrode gap. The base sequence is determined based on the change in the tunnel current. This technique is anticipated to have the potential to provide a very low-cost and very compact-size apparatus that is capable of analyzing a base sequence. It should be noted that, in the present specification, examples of such a "nano-electrode" include sub-micro electrodes and micro electrodes having a larger size.

Also, as a method using a tunnel current in the same way as with the gating nanopore sequencing technique, the MCBJ (Mechanically Controllable Break Junction) method has been developed. With the MCBJ method, a nano-electrode is formed by breaking a metal wire.

As an important element technology, such a sequencer requires a current measurement device that is capable of measuring a tunnel current that flows through a nano-electrode gap with sufficiently high precision. That is to say, such a tunnel current has a current value on the order of several tens of pA. Accordingly, in order to judge the base type, there is a need to detect a difference in conductance on the order of several ps (picosecond).

The present inventors have investigated an arrangement employing a transimpedance amplifier as a microscopic current measurement device. FIG. 1 is a circuit diagram showing a current measurement circuit 900 including a transimpedance amplifier 800. The transimpedance amplifier 800 includes an operational amplifier 802 and a resistor $R_F$ arranged between the inverting input terminal (−) and the output terminal of the operational amplifier 802. A predetermined electric potential $V_{REF}$ (e.g., ground voltage) is input to the non-inverting input terminal (+) of the operational amplifier 802. A capacitor $C_F$ is connected in parallel with the resistor $R_F$, in order to provide the circuit with stable operation.

A DUT (device under test) 810 includes a sample such as DNA, RNA, or the like (which will collectively be referred to as "DNA" hereafter), and a chip configured to house the sample. A nanochannel, nanopillar structure, and an electrode pair are formed in the chip such that a DNA molecule separated from the sample passes through such components. A cable 820 connects the DUT 810 and the transimpedance amplifier 800.

FIG. 2 is an equivalent circuit diagram showing an equivalent circuit of the current measurement circuit 900 shown in FIG. 1. The DUT 810 can be modeled as a circuit comprising a current source 812 that generates a tunnel current $i_{DUT}$, a parasitic parallel resistor $R_{DUT}$, and a parasitic parallel capacitor $C_{DUT}$.

The cable 820 includes a first line 822 that connects one end 814 of the DUT 810 and the inverting input terminal of the operational amplifier 802, and a second line 824 that connects the other end 816 of the DUT 810 and the non-inverting input terminal of the operational amplifier 802. Here, $C_{CAB}$ represents a parasitic capacitance that occurs between the two lines 822 and 824. In a case in which the cable 820 is configured as a coaxial cable, a parasitic capacitance of 10 pF occurs in increments of 10 cm of the cable 820.

Various kinds of parasitic capacitances occur in the input stage of the transimpedance amplifier 800. For example, $C_{PRO}$ represents a parasitic capacitance that occurs due to an ESD protection element 830 such as a diode, ESD suppresser, or the like. The operational amplifier 802 is represented by an equivalent circuit comprising an ideal amplifier 804 and various kinds of parasitic capacitances. Here, CMN and CMP each represent a common input capacitance, and CD represents a differential input capacitance. It should be noted that, in FIG. 2, the resistance values and capacitance values are shown for exemplary purposes only.

The DC transimpedance of the transimpedance amplifier 800 is represented by the following Expression.

$$20 \times \log_{10}(R_F)(\text{dB}) \tag{1}$$

For example, in a case in which $R_F$=1 GΩ, the transimpedance amplifier 800 has a DC transimpedance of 180 dB.

Such a DNA sequencer is required to identify the kinds of bases with respect to an enormous number of base pairs, the number of which is on the order of several billion. A fourth-generation DNA sequencer is required to provide a measurement time on the order of 1 ms per base. However, it is difficult for such a fourth-generation DNA sequencer to identify a base based on a single measurement due to the influence of noise. Thus, the tunnel current is measured multiple times during the measurement time of 1 ms, and the base is identified using a statistical method. Specifically, the base is identified based on a histogram of the measurement results, for example. For example, in a case in which the tunnel current is measured 100 times during the measurement time of 1 ms, such an arrangement requires a sampling rate of 100 ksps. In this case, the transimpedance amplifier is required to have a bandwidth of several hundreds of kHz to several MHz, which is estimated giving consideration to a margin.

Here, examination will be made regarding the frequency characteristics of the transimpedance amplifier 800 shown in FIG. 2. The cutoff frequency f2 is represented by the following Expression (2).

$$f2 = 1/\{2\pi R_F \times (C_F + C_S/A_{OL})\} \tag{2}$$

It should be noted that $C_S$ is represented by $C_S = C_{DUT} + C_{CAB} + C_{PRO} + CD$. Here, $A_{OL}$ represents the open loop gain of the operational amplifier. As can be understood from Expression (2), in order to raise the cutoff frequency f2, an approach can be employed in which $C_F$ and $C_S$ are each reduced, and $A_{OL}$ is raised over a wide bandwidth. Here, $C_S$ will be referred to as "input shunt capacitance". In a case in which the open loop gain $A_{OL}$ is sufficiently large, and the input shunt capacitance $C_S$ is sufficiently small, Expression (2) is approximated by the following Expression (3).

$$f2 \approx 1/\{2\pi R_F \times C_F\} \quad (3)$$

For example, in a case in which $R_F=1$ GΩ, and $C_F=10$ fF, f2=15.9 kHz is obtained based on Expression (3).

However, the tunnel current has a very small current value. Thus, such a tunnel current is affected by measurement system noise, which is a problem. FIG. 3 is a diagram showing the noise characteristics of the transimpedance amplifier. In order to detect such a microscopic current, such an arrangement requires a resistor $R_F$ on the order of several tens of MΩ to several TΩ. Accordingly, in the low-frequency range, thermal noise due to the resistor $R_F$ becomes dominant.

$$V_{NOISE} = \sqrt{(4 \times k \times T \times R_F)}$$

Here, T represents the temperature, and k represents the Boltzmann constant. This expression represents the voltage noise density per unit frequency.

In a case in which $R_F=1$ GΩ, and T=27 degrees, $V_{NOISE}=4.1$ μV/√Hz (which is also represented by "V/rtHz") is obtained.

The transimpedance amplifier 800 imposes a band limit on the thermal noise with the aforementioned cutoff frequency f2 as the boundary. Thus, in the high-frequency range that is higher than the cutoff frequency f2, the noise from the transimpedance amplifier 800 becomes dominant as compared with the thermal noise that occurs in the resistor $R_F$. In the high-frequency range, the noise gain of the amplifier is proportional to $(C_F+C_S+CM+CD)/C_F$. Thus, in order to reduce the noise, $C_S$, CM, and CD must be reduced, and $C_F$ must be raised. However, an increase in $C_F$ leads to a reduction in the cutoff frequency f2, which is opposite to a requirement of increasing the bandwidth. Thus, there is a need to design the capacitor $C_F$ to have as small a value as possible in a range so as to ensure system stability. As described above, with the transimpedance amplifier shown in FIG. 1, there is a tradeoff relation between the bandwidth (cutoff frequency) to be raised and the noise to be reduced. That is to say, it is difficult to provide both a wide bandwidth and low noise.

In particular, the operational amplifier has a very high input impedance. Accordingly, the transimpedance amplifier is greatly affected by electric-field noise. In order to reduce such noise, a technique is known in which the signal line is covered by a shield, and the electric potential at the shield is controlled. However, in a case in which such a shield is provided as an additional component to the transimpedance amplifier which is required to provide a high-speed operation, this leads to an increase in the parasitic capacitance due to the signal line. In addition, an amplifier that drives the shield involves a capacitance. Thus, such an arrangement leads to a narrow bandwidth and a reduced operation speed.

SUMMARY OF THE INVENTION

The present invention has been made in order to solve such a problem. Accordingly, it is an exemplary purpose of an embodiment of the present invention to provide a current measurement circuit which provides reduced noise and/or a widened bandwidth.

An embodiment of the present invention relates to a current measurement circuit that converts a current signal into a voltage signal. The current measurement circuit comprises: a signal line via which the current signal is transmitted; a shield line arranged in the vicinity of at least a part of the signal line; a non-inverting amplifier comprising an operational amplifier having its non-inverting input terminal supplied with the current signal the signal line and its inverting input terminal supplied with its output signal as a feedback signal; an inverting amplifier that amplifies the output signal of the non-inverting amplifier with inversion so as to generate the voltage signal; an impedance circuit comprising a feedback resistor arranged between an output terminal of the inverting amplifier and the non-inverting input terminal of the operational amplifier; and a guard amplifier that receives an electric potential at the inverting input terminal of the operational amplifier, and that applies the electric potential to the shield line.

By providing a two-stage configuration comprising the non-inverting amplifier and the inverting amplifier, such an arrangement is capable of reducing the effect of the differential input capacitance that occurs in the operational amplifier included in the non-inverting amplifier configured as a first-stage amplifier. Furthermore, by providing the shield line in the vicinity of the signal line, such an arrangement is capable of reducing the capacitance that occurs between the signal line and the ground. With such an arrangement, by virtually grounding the operational amplifier, the electric potential at the inverting input terminal of the operational amplifier becomes substantially the same as that at the non-inverting input terminal thereof. The signal line is connected to the non-inverting input terminal of the operational amplifier. Furthermore, the electric potential at the inverting input terminal of the operational amplifier is applied to the shield line via the guard amplifier. Thus, the electric potential at the signal line becomes substantially the same as that at the shield line. This allows the effects of the capacitance that occurs between the signal line and the shield line to be reduced. Furthermore, the input of the guard amplifier is connected to the inverting input terminal of the operational amplifier included in the non-inverting amplifier. Thus, the input capacitance that occurs in the guard amplifier is not coupled with the signal line. Thus, such an arrangement does not lead to an increase in the capacitance as viewed from the signal line. That is to say, it can be said that the effect of the guard amplifier on the cutoff frequency is substantially zero.

Thus, such an embodiment is capable of greatly reducing the effects of the parasitic capacitance as viewed from the signal line, thereby reducing the noise gain. Furthermore, by providing such a two-stage amplifier configuration, such an arrangement provides a high gain over a wide bandwidth while suppressing an increase in noise.

Also, the current measurement circuit may further comprise a correction amplifier that corrects frequency characteristics of an output signal of the inverting amplifier.

As described above, by providing such a two-stage configuration comprising the non-inverting amplifier and the inverting amplifier, such an arrangement is capable of providing reduced noise gain in a high-frequency range. Thus, by providing the correction amplifier that boosts such a high-frequency signal component, such an arrangement provides a high signal gain over a wide bandwidth while maintaining the noise gain at the same level as that provided by conventional arrangements.

Also, the current measurement circuit may further comprise a shield that covers at least a part of the feedback resistor. Also, an output of the guard amplifier may be connected to the shield.

In an equivalent circuit, the parasitic capacitance that couples with the feedback resistor is connected to the signal line. With such an embodiment, by shielding the feedback resistor, and by supplying an electric potential to the shield by means of the guard amplifier, such an arrangement is capable of reducing the effects of the floating capacitance that couples with the feedback resistor.

Also, the shield may cover one electrode, which is arranged on an input terminal side of the non-inverting amplifier, of the feedback resistor having two electrodes. Such an arrangement is capable of reducing the floating capacitance that occurs between the shield and one terminal, which is arranged on the output terminal side of the inverting amplifier, of the feedback resistor having two electrodes.

Also, the current measurement circuit may further comprise a protection element arranged between the signal line and the shield line.

This also allows the effects of the parasitic capacitance that occurs due to the protection element to be reduced.

Also, the signal line and the shield line are configured as a cable having a hollow coaxial cable structure or otherwise a low-capacitance coaxial cable structure. This allows the parasitic capacitance that occurs between the signal line and the shield line to be reduced.

Also, the current measurement circuit may be integrated on a semiconductor substrate together with a part of a device under test that generates the current signal. Also, the signal line and the shield line may be formed on the semiconductor substrate. This allows the parasitic capacitance that occurs between the signal line and the shield line to be reduced.

Also, the impedance circuit may further comprise a feedback capacitor arranged in parallel with the feedback resistor between an output terminal of the inverting amplifier and the non-inverting input terminal of the non-inverting amplifier. Such an arrangement provides improvement of the stability of the system.

Another embodiment of the present invention relates to a base sequence analyzing apparatus. The base sequence analyzing apparatus comprises: an electrode pair; a position control apparatus that controls a base sequence having a linear structure such that it passes through the electrode pair; any one of the aforementioned current measurement circuits that detect a current that flows between a gap of the electrode pair; and a data processing apparatus that analyzes an output of the current measurement circuit.

Such an embodiment provides high-speed operation of the transimpedance amplifier. Thus, such an arrangement allows the number of times each base is sampled to be increased, thereby providing improved measurement precision. Alternatively, such an arrangement allows the number of bases that can be analyzed per unit time to be increased.

It is to be noted that any arbitrary combination or rearrangement of the above-described structural components and so forth is effective as and encompassed by the present embodiments.

Moreover, this summary of the invention does not necessarily describe all necessary features so that the invention may also be a sub-combination of these described features.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

The invention will now be described based on preferred embodiments which do not intend to limit the scope of the present invention but exemplify the invention. All of the features and the combinations thereof described in the embodiment are not necessarily essential to the invention.

In the present specification, the state represented by the phrase "the member A is connected to the member B" includes a state in which the member A is indirectly connected to the member B via another member that does not affect the electric connection therebetween, in addition to a state in which the member A is physically and directly connected to the member B.

Similarly, the state represented by the phrase "the member C is provided between the member A and the member B" includes a state in which the member A is indirectly connected to the member C, or the member B is indirectly connected to the member C via another member that does not affect the electric connection therebetween, in addition to a state in which the member A is directly connected to the member C, or the member B is directly connected to the member C.

First Embodiment

Figure 4:
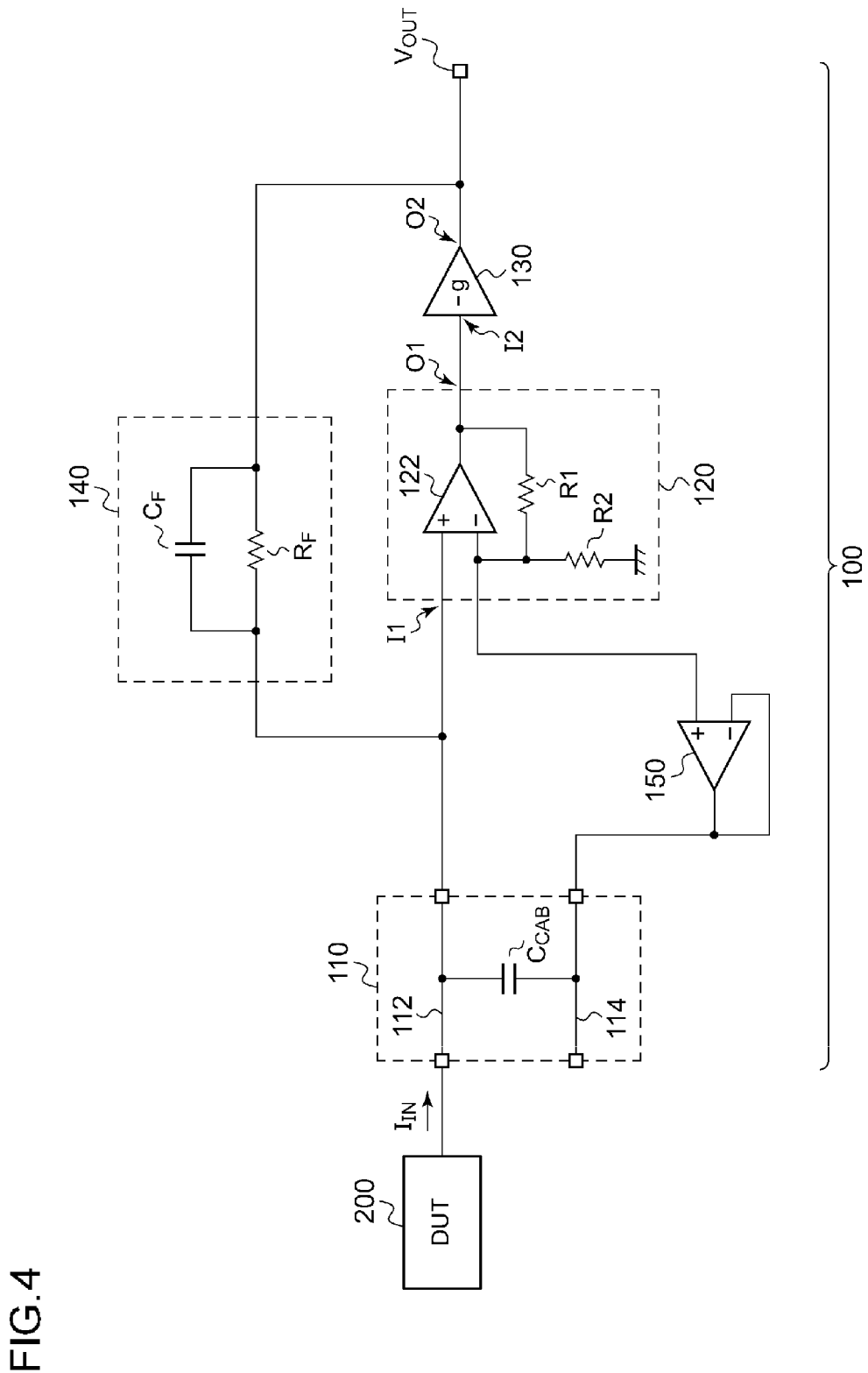
FIG. 4 is a circuit diagram showing a current measurement circuit according to a first embodiment.

FIG. 4 is a circuit diagram showing a current measurement circuit 100 according to a first embodiment. The current measurement circuit 100 converts a current signal $I_{IN}$ output from a DUT 200 into a voltage signal $V_{OUT}$. The current measurement circuit 100 includes a cable 110, a non-inverting amplifier 120, an inverting amplifier 130, an impedance circuit 140, and a guard amplifier 150.

A signal line 112 is configured as a path via which the current signal $I_{IN}$ is transmitted. The signal line 112 is arranged such that one end thereof is connected to a DUT 200 and the other end thereof is connected to an input terminal I1 of the non-inverting amplifier 120. A shield line 114 is arranged in the vicinity of at least a part of the signal line 112. At least a part of the signal line 112 and at least a part of the shield line 114 may be housed in the same cable 110. It should be noted that the state represented by "the signal line and the shield line are arranged in the vicinity of each other" represents a state in which the signal line and the shield line are arranged within a range of distance in which a parasitic capacitance that occurs between the signal line and the shield line has a significant effect on the gain and the frequency characteristics of the current measurement circuit. Specifically, such a distance is on the order of several hundreds of μm to several hundreds of mm.

Figure 5A:
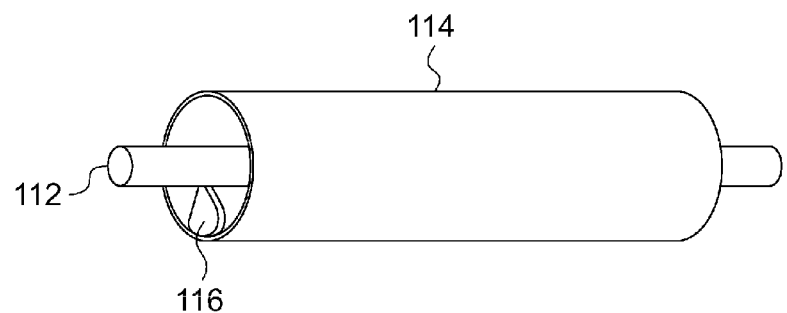
FIGS. 5A through 5C are diagrams each showing a configuration of a cable.
Figure 5B:
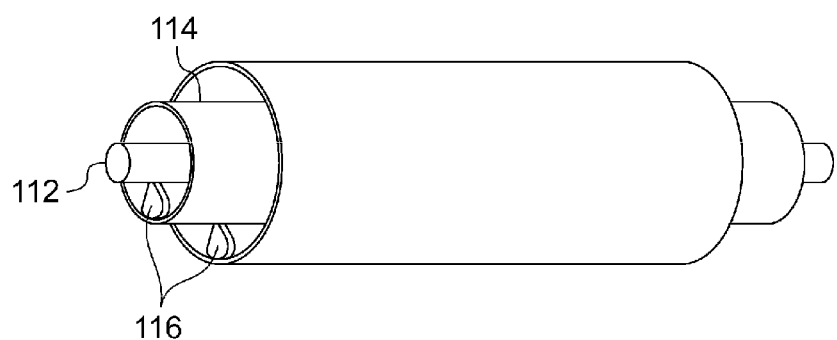
Figure 5C:
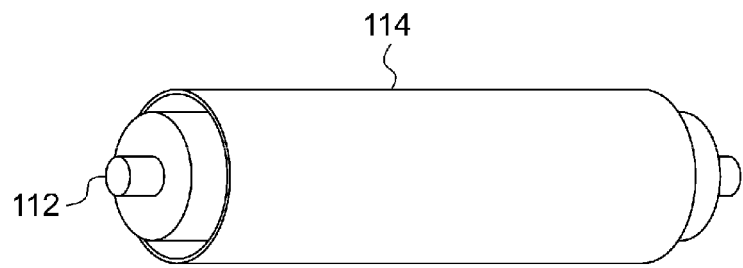

FIGS. 5A through 5C are diagrams each showing a configuration of the cable 110. For example, the cable 110 may be configured as a hollow coaxial cable as shown in FIG. 5A. Also, the cable 110 may be configured as a hollow triaxial cable as shown in FIG. 5B. Also, the cable 110 may be configured as a low-capacitance coaxial cable as shown in FIG. 5C. With the hollow coaxial cable shown in FIG. 5A or 5B, the cable core configured as the signal line 112 is supported by a support member 116 formed of a Teflon (trademark) material or the like with respect to an electrically conducting pipe configured as the shield line 114. By employing such a cable, such an arrangement allows the absolute value of the parasitic capacitance that occurs between the signal line 112 and the shield line 114 to be reduced.

Returning to FIG. 4, the non-inverting amplifier 120 amplifies the electric potential at its input terminal I1 without inversion, and outputs the output signal via its output terminal O1. The non-inverting amplifier 120 includes an operational amplifier 122. The operational amplifier 122 is arranged such that its non-inverting input terminal (+) is connected to the signal line 112, and its inverting input terminal (−) receives its output signal O1 as a feedback signal. More specifically, an output signal obtained by dividing the output signal O1 by means of resistors R1 and R2 is fed back to the inverting input terminal of the operational amplifier 122. The gain of the non-inverting amplifier 120 is represented by (R1+R2)/R2. Also, the non-inverting amplifier 120 may be configured to have a gain on the order of 100 (40 dB).

The inverting amplifier 130 amplifies the output signal O1 of the non-inverting amplifier 120 with inversion so as to generate an output voltage $V_{OUT}$, and outputs the generated output voltage $V_{OUT}$ via its output terminal O2. The open loop gains $A_{OL}$ of the non-inverting amplifier 120 and the inverting amplifier 130 are preferably set to values on the order of 60 to 80 dB. The non-inverting amplifier 120 and the inverting amplifier 130 are each configured to have an appropriate gain.

The impedance circuit 140 includes a feedback resistor $R_F$ arranged between the output terminal O2 of the inverting amplifier 130 and the input terminal I1 of the non-inverting amplifier (non-inverting input terminal of the operational amplifier 122). Furthermore, the feedback capacitor $C_F$ is arranged in parallel with the feedback resistor $R_F$.

The guard amplifier 150 receives the electric potential V− at the inverting input terminal (−) of the operational amplifier 122, and stabilizes the electric potential at the shield line 114 to be the same as the electric potential V− at the inverting input terminal of the operational amplifier 122. The guard amplifier 150 may be configured as a voltage follower. Also, the guard amplifier 150 may have other configurations.

Figure 6:
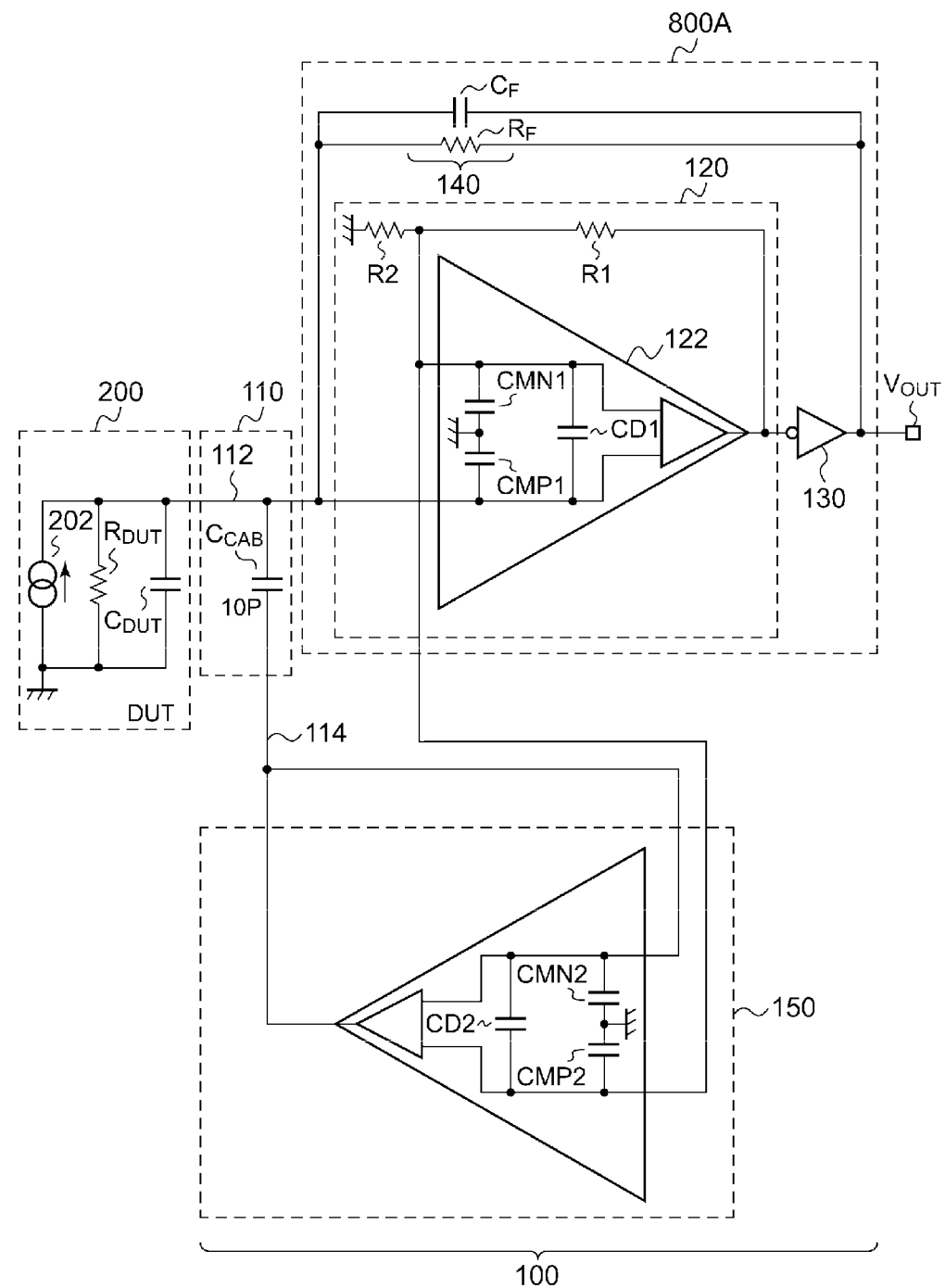
FIG. 6 is an equivalent circuit diagram showing the current measurement circuit shown in FIG. 4.

The above is the configuration of the current measurement circuit 100. FIG. 6 is an equivalent circuit diagram showing the current measurement circuit 100 shown in FIG. 4. The advantages of the current measurement circuit 100 can be clearly understood in comparison with the equivalent circuit diagram in FIG. 6 and the equivalent circuit diagram in FIG. 2. It should be noted that a circuit block 800A shown in FIG. 6 including the non-inverting amplifier 120, the inverting amplifier 130, and the impedance circuit 140 corresponds to the transimpedance amplifier 800 shown in FIG. 2. As further seen in FIG. 6, the DUT 200 can be modeled as a circuit comprising a current source 202 that generates a tunnel current $i_{DUT}$, a parasitic parallel resistor $R_{DUT}$, and a parasitic parallel capacitor $C_{DUT}$. Additionally, the operational amplifier 122 of the non-inverting amplifier 120 included common input capacitances CMN1 and CMP1 at its input.

Figure 2:
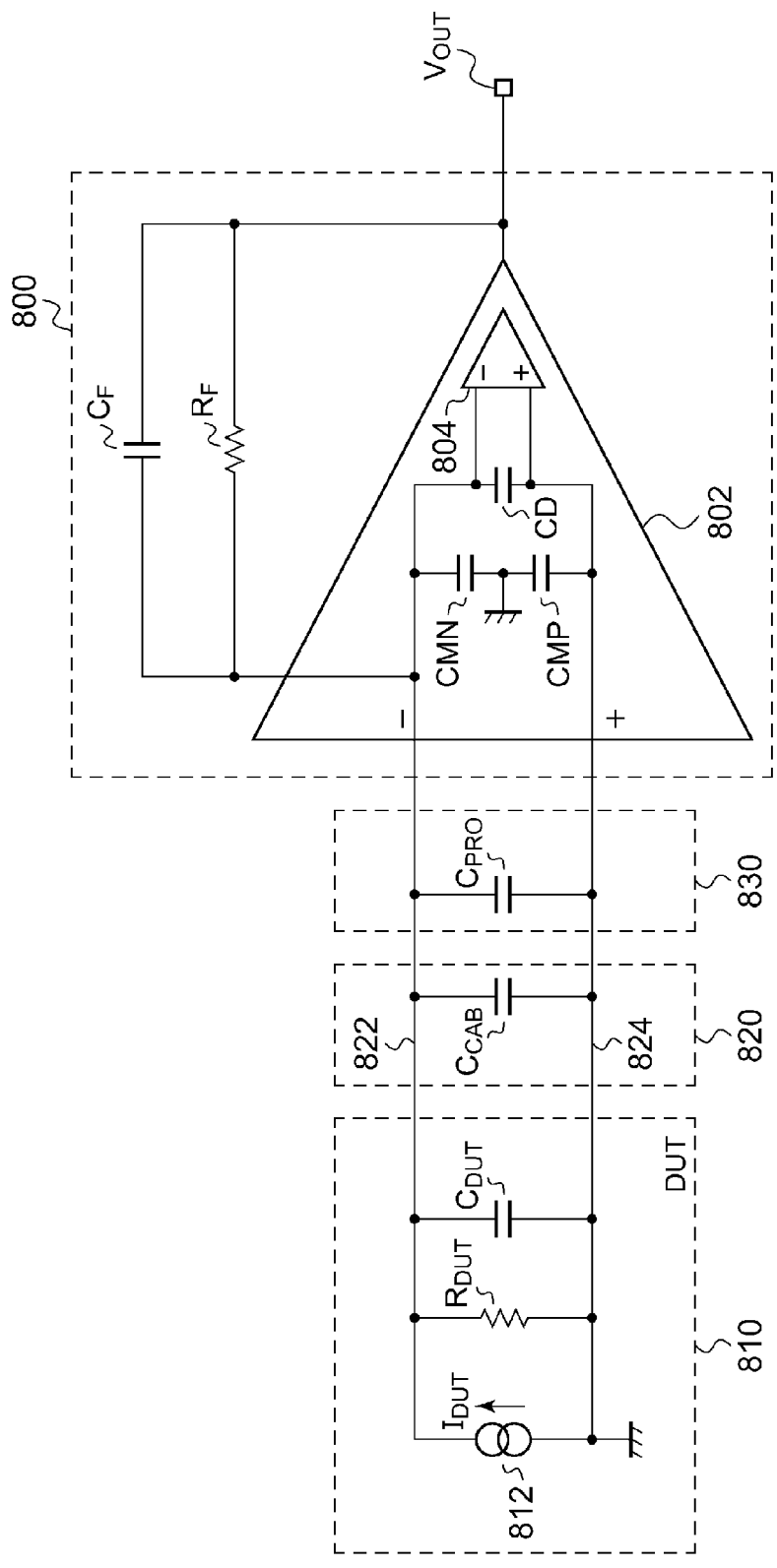
FIG. 2 is an equivalent circuit diagram showing the current measurement circuit shown in FIG. 1;
Drawings.
Figure 3:
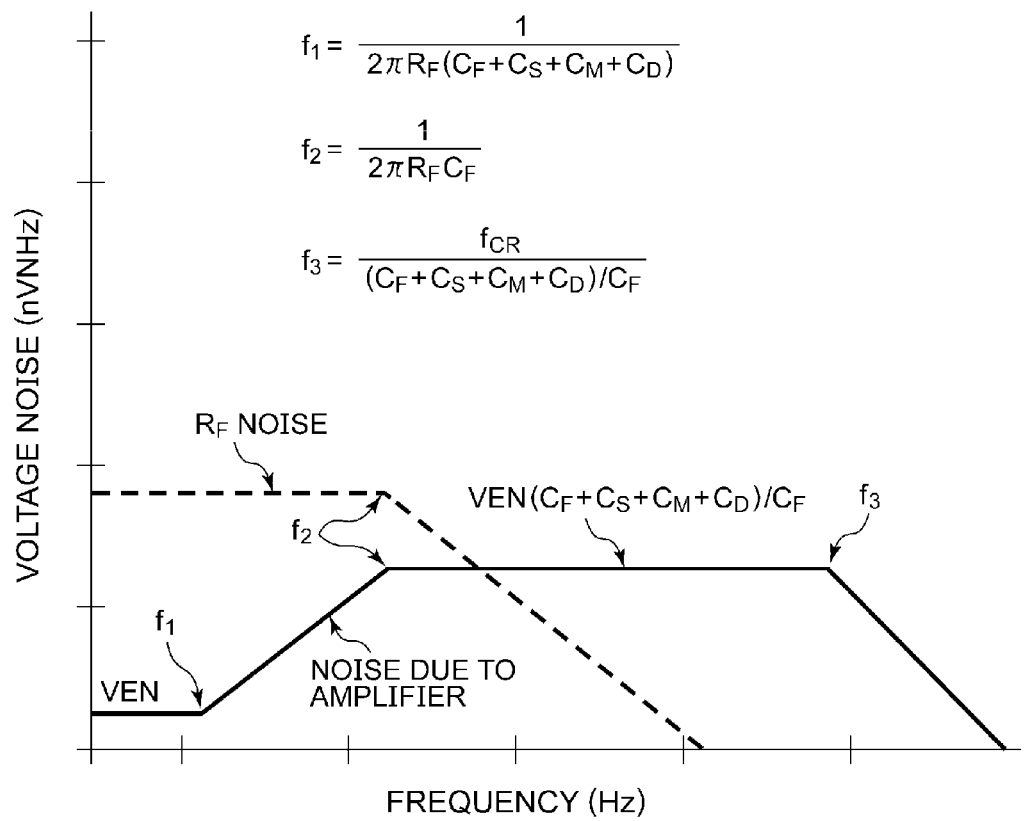
FIG. 3 is a diagram showing the noise characteristics of the transimpedance amplifier.

The current measurement circuit 100 has a two-stage configuration comprising the non-inverting amplifier 120 and the inverting amplifier 130. In FIG. 2, the differential input capacitance CD of the operational amplifier 802 is connected in parallel with the cable capacitance $C_{CAB}$ or the like, which functions as a part of the input shunt capacitance $C_S$. This leads to a reduction in the cutoff frequency f2 of the transimpedance amplifier 800. In contrast, with the equivalent circuit shown in FIG. 6, the differential input capacitance CD1 of the operational amplifier 122 is not arranged in parallel with the cable capacitance $C_{CAB}$ or the like. Thus, such an arrangement is capable of preventing the cutoff frequency f2 of the transimpedance amplifier 800A from degrading due to the differential input capacitance CD1.

Furthermore, by arranging the shield line 114 in the vicinity of the signal line 112, such an arrangement is capable of reducing the capacitance that occurs between the signal line 112 and the ground. This allows the input shunt capacitance $C_S$ to be reduced.

Furthermore, by virtually grounding the operational amplifier 122, the electric potential at the inverting input terminal (−) of the operational amplifier 122 becomes substantially the same as that at the non-inverting input terminal (+) thereof. With such an arrangement, the signal line 112 is connected to the non-inverting input terminal (+) of the operational amplifier 122. Furthermore, the electric potential at the inverting input terminal (−) of the operational amplifier 122 is applied to the shield line 114 via the guard amplifier 150. Thus, the electric potential at the signal line 112 becomes substantially the same as that at the shield line 114. With such an arrangement, the voltage difference between the signal line 112 and the shield line 114 is maintained at a given value (substantially at 0 V) even if they fluctuate. Thus, the parasitic capacitance $C_{CAB}$ is neither charged nor discharged. Thus, in the equivalent circuit, the parasitic capacitance $C_{CAB}$ becomes zero, thereby reducing the effect of the parasitic capacitance $C_{CAB}$.

Furthermore, with the present embodiment, the input terminal of the guard amplifier 150 is connected to the inverting input terminal (−) of the operational amplifier 122 of the non-inverting amplifier 120, instead of being connected to the non-inverting input terminal (+) thereof. With such an arrangement, the input capacitances CMN2, CMP2, and CD2 of the guard amplifier 150 are not coupled with the signal line 112. Thus, such input capacitances do not lead to an increase in the capacitance $C_S$ as viewed from the signal line 112. That is to say, it can be said that the guard amplifier 150 has substantially no effect on the cutoff frequency f2.

Figure 7A:
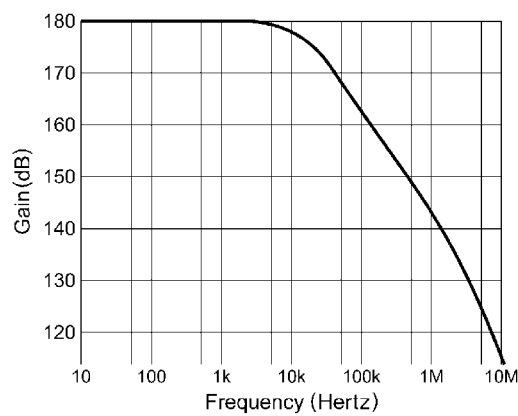
FIG. 7A is a diagram showing the frequency characteristics of the current measurement circuit shown in FIG. 4.
Figure 7B:
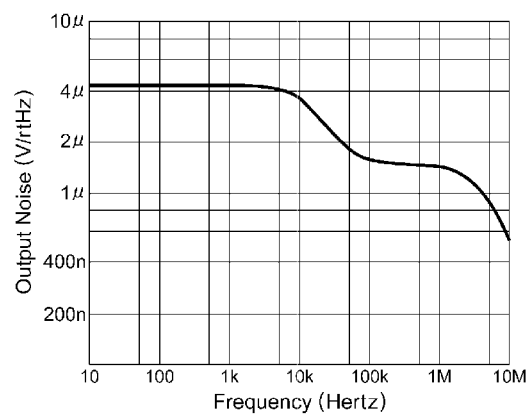
FIG. 7B is a diagram showing the noise characteristics of the current measurement circuit shown in FIG. 4.

FIG. 7A is a diagram showing the frequency characteristics of the current measurement circuit 100 shown in FIG. 4. FIG. 7B is a diagram showing the noise characteristics of the current measurement circuit 100 shown in FIG. 4. The frequency characteristics and the noise characteristics were calculated by simulation.

Figure 1:
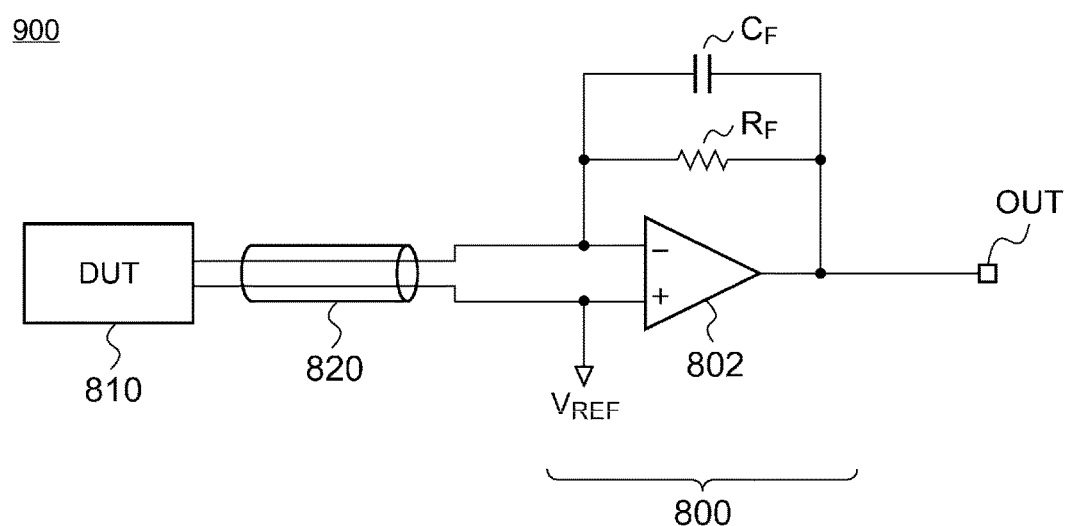
FIG. 1 is a circuit diagram showing a current measurement circuit including a transimpedance amplifier.

As shown in FIG. 7B, the current measurement circuit 100 is capable of greatly reducing the effect of the parasitic capacitance $C_S$ as viewed from the signal line 112, as compared with an arrangement shown in FIG. 1. This allows the noise gain to be reduced.

As a comparison technique, another two-stage configuration is conceivable in which the first stage is configured as a voltage follower having a gain of 1, and the second stage is configured as a high-gain amplifier. However, it is difficult for the second-stage amplifier to secure a sufficient open loop gain $A_{OL}$ over a wide bandwidth. Furthermore, such a configuration leads to a problem of increased noise, and leads to difficulty in maintaining stable operation of the system. With the current measurement circuit 100 according to the embodiment, the transimpedance amplifier 800A has a two-stage configuration comprising the non-inverting amplifier 120 and the inverting amplifier 130. Furthermore, by configuring the first-stage amplifier, i.e., the non-inverting amplifier 120, to have a high gain, such an arrangement provides the transimpedance amplifier 800A with a high gain over a wide bandwidth while suppressing an increase in noise.

Second Embodiment

Figure 8:
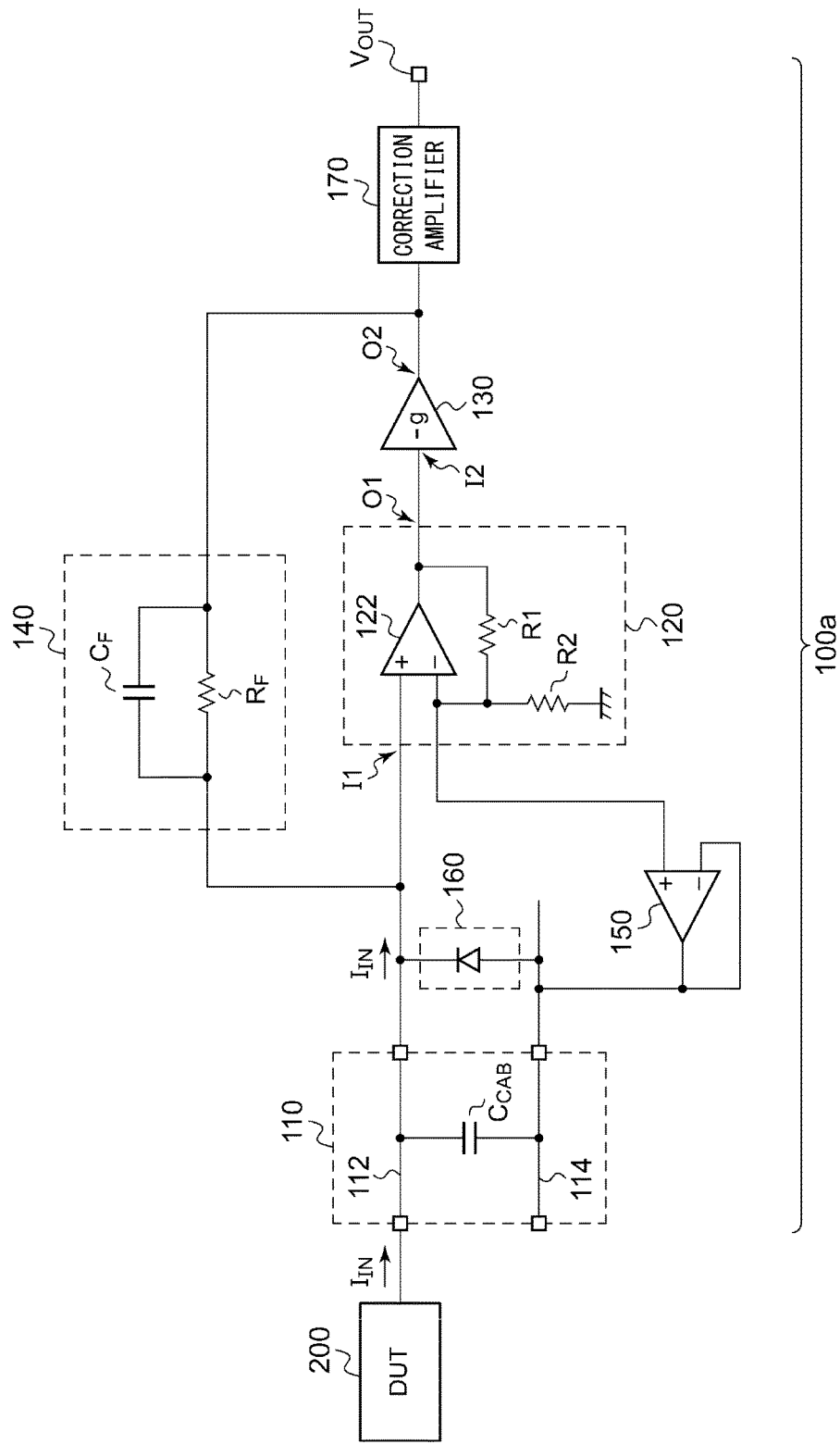
FIG. 8 is a circuit diagram showing a current measurement circuit according to a second embodiment.

FIG. 8 is a circuit diagram showing a current measurement circuit 100a according to a second embodiment. The current measurement circuit 100a further includes a protection element 160 and a correction amplifier 170 in addition to the components included in the current measurement circuit 100 shown in FIG. 4. Typically, such a protection element 160 is arranged between the signal line 112 and the ground line. However, in the present embodiment, the protection element 160 is arranged between the signal line 112 and the shield line 114.

With such an arrangement, as with the parasitic capacitance $C_{CAB}$ that occurs due to the cable 110, a parasitic capacitance $C_{PRO}$ that occurs due to the protection element 160 becomes substantially zero as viewed from the signal line 112. That is to say, such an arrangement allows the effects of the parasitic capacitance $C_{PRO}$ to be reduced. Thus, such an arrangement is capable of preventing an increase in the capacitance $C_S$ connected to the signal line 112 even in a case in which such a protection element 160 is provided.

Figure 9A:
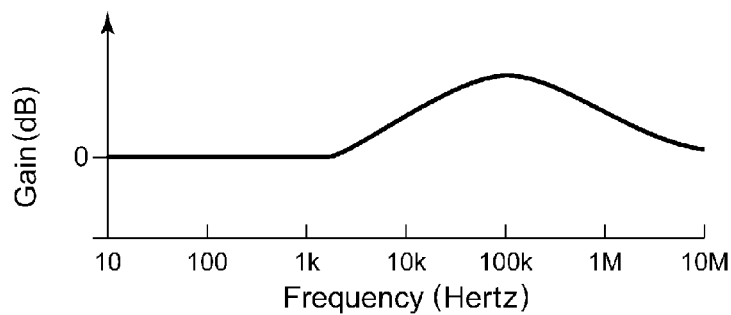
FIG. 9A is a diagram showing the frequency characteristics of a correction amplifier.
Figure 9B:
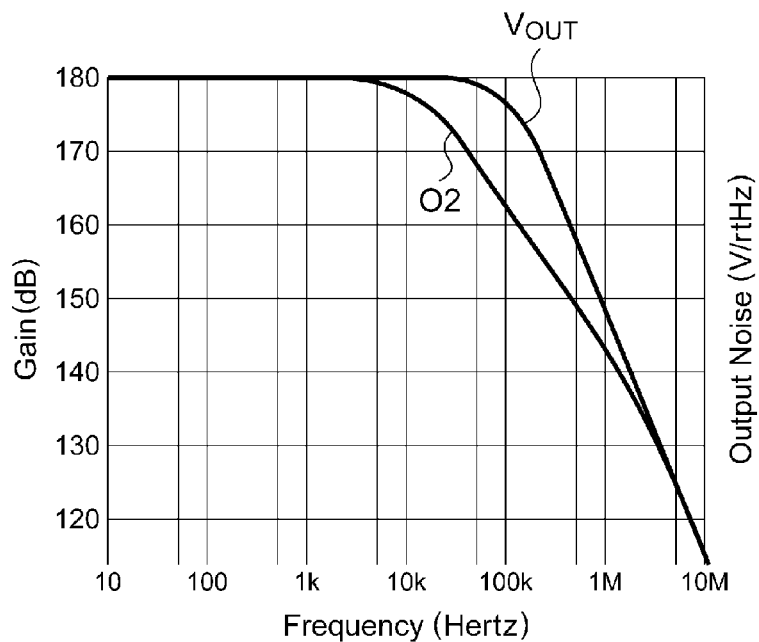
FIG. 9B is a diagram showing the frequency characteristics of the current measurement circuit.
Figure 9C:
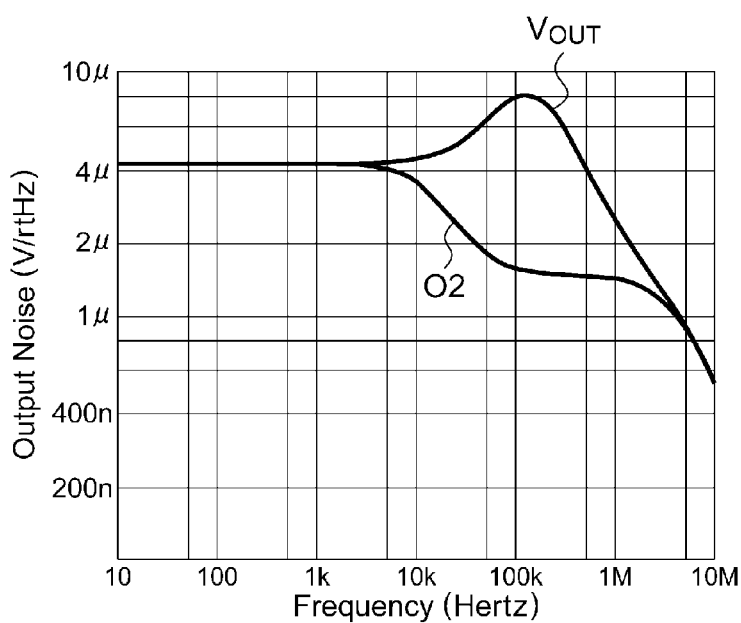
FIG. 9C is a diagram showing the noise characteristics of the current measurement circuit.

The correction amplifier 170 corrects the frequency characteristics of the output signal O2 output from the inverting amplifier 130, and outputs an output voltage $V_{OUT}$. FIG. 9A is a diagram showing the frequency characteristics of the correction amplifier 170. FIG. 9B is a diagram showing the frequency characteristics of the current measurement circuit 100a of FIG. 8. FIG. 9C is a diagram showing the noise characteristics of the current measurement circuit 100a of FIG. 8. A specific configuration of the correction amplifier 170 is not restricted in particular. Such a correction amplifier 170 may preferably be configured as a known high-emphasis filter or the like.

As shown in FIG. 7B, the transimpedance amplifier 800A has a two-stage configuration comprising the non-inverting amplifier 120 and the inverting amplifier 130 so as to reduce the capacitance C. This reduces the noise gain of the transimpedance amplifier 800A in a high-frequency range. Thus, by boosting the high-frequency component by means of the correction amplifier 170, such an arrangement provides a sufficiently high signal gain over a wide bandwidth while maintaining the noise gain at the same level as that provided by conventional arrangements. FIG. 9A shows a case in which the bandwidth is widened from a value on the order of 10 kHz to 100 kHz.

It should be noted that the protection element 160 or otherwise the correction amplifier 170 may be omitted from the current measurement circuit 100a shown in FIG. 8. Also, such an arrangement is effective as an embodiment of the present invention.

Third Embodiment

Figure 10:
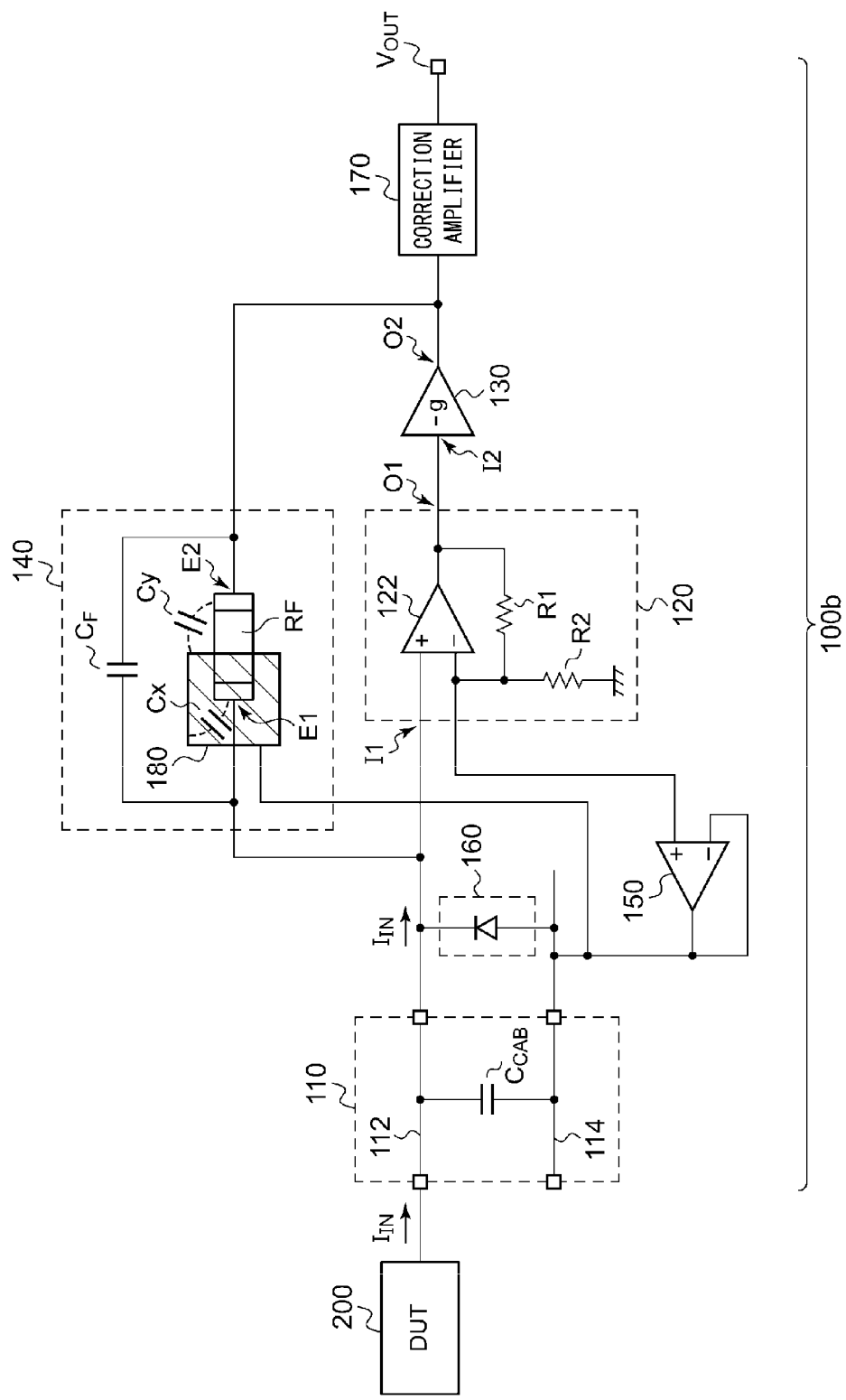
FIG. 10 is a circuit diagram showing a current measurement circuit according to a third embodiment.

FIG. 10 is a circuit diagram showing a current measurement circuit 100b according to a third embodiment. The current measurement circuit 100b further includes a shield 180 in addition to the components of the current measurement circuit 100a shown in FIG. 8. The feedback resistor $R_F$ is configured as a chip element or otherwise an SIP (Single Inline Package) element. The feedback resistor $R_F$ includes a pair of exposed electrodes E1 and E2. The shield 180 is arranged such that it covers at least a part of the feedback resistor $R_F$. The shield 180 is preferably arranged such that it covers the electrode E1 of the feedback resistor $R_F$ on the input side of the non-inverting amplifier 120. The output of the guard amplifier 150 is electrically connected to the shield 180. The electric potential at the inverting input terminal of the operational amplifier 122 is applied to the shield 180.

In an equivalent circuit of the current measurement circuit 100b, the coupling of the floating capacitances Cx and Cy to the feedback resistor $R_F$ is connected to the signal line 112. With the current measurement circuit 100b, by shielding the feedback resistor $R_F$, and by supplying the same electric potential as that at the signal line 112 to the shield by means of the guard amplifier 150, such an arrangement is capable of reducing the effects of the coupling of the floating capacitances Cx and Cy to the feedback resistor $R_F$.

Furthermore, by configuring the shield 180 such that it covers only the electrode E1 on the input terminal side of the non-inverting amplifier 120, such an arrangement allows the floating capacitance Cy that occurs due to the electrode E2 on the output terminal side to be reduced. Such an arrangement is capable of preventing the bandwidth from narrowing.

Description has been made regarding the present invention with reference to the embodiment. The above-described embodiment has been described for exemplary purposes only, and is by no means intended to be interpreted restrictively. Rather, it can be readily conceived by those skilled in this art that various modifications may be made by making various combinations of the aforementioned components or processes, which are also encompassed in the technical scope of the present invention. Description will be made below regarding such modifications.

First Modification

Figure 11A:
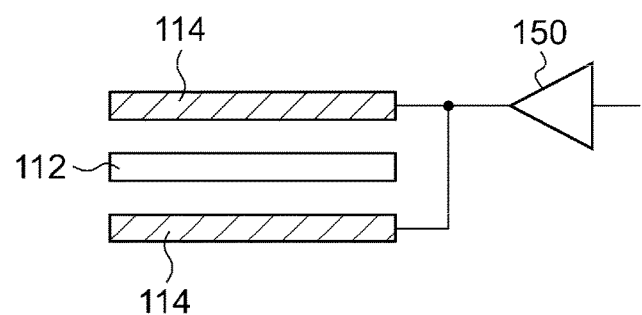
FIGS. 11A and 11B are diagrams each showing a part of a current measurement circuit according to a first modification.
Figure 11B:
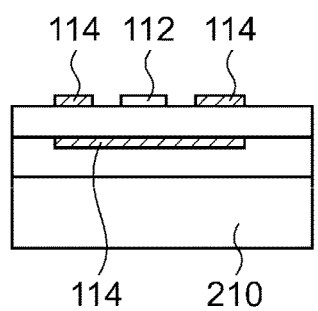

Description has been made in the embodiments regarding an arrangement in which a part of the signal line 112 and a part of the shield line 114 are housed in the cable 110. However, the present invention is not restricted to such an arrangement. FIGS. 11A and 11B are diagrams each showing a part of a current measurement circuit 100c according to a first modification.

In this modification, the current measurement circuit 100c is integrated on a single semiconductor substrate 210 together with a part of the device under test 200 that generates the current signal $I_{IN}$. Such an arrangement does not require the cable 110. The signal line 112 and the shield line 114 are each formed as an LSI line on the semiconductor substrate 210. FIG. 11A is a plan view of the current measurement circuit 100c. The shield line 114 may be formed adjacent to the signal line 112. More preferably, the shield lines 114 may be formed such that the signal line 112 is interposed between them. FIG. 11B is a cross-sectional view of the current measurement circuit 100c. Also, such a shield line 114 may be formed in a wiring layer adjacent to that including the signal line 112 such that they overlap. Also, such a shield line 114 may be formed in an upper wiring layer adjacent to that including the signal line 112.

Such a modification allows the parasitic capacitance $C_{CAB}$ that occurs between the signal line 112 and the shield line 114 to be reduced, as compared with an arrangement employing the cable 110.

Second Modification

The configuration of the impedance circuit 140 is not restricted to such an arrangement as described in the embodiments. Also, various kinds of other configurations may be employed.

[Usage]

Figure 12:
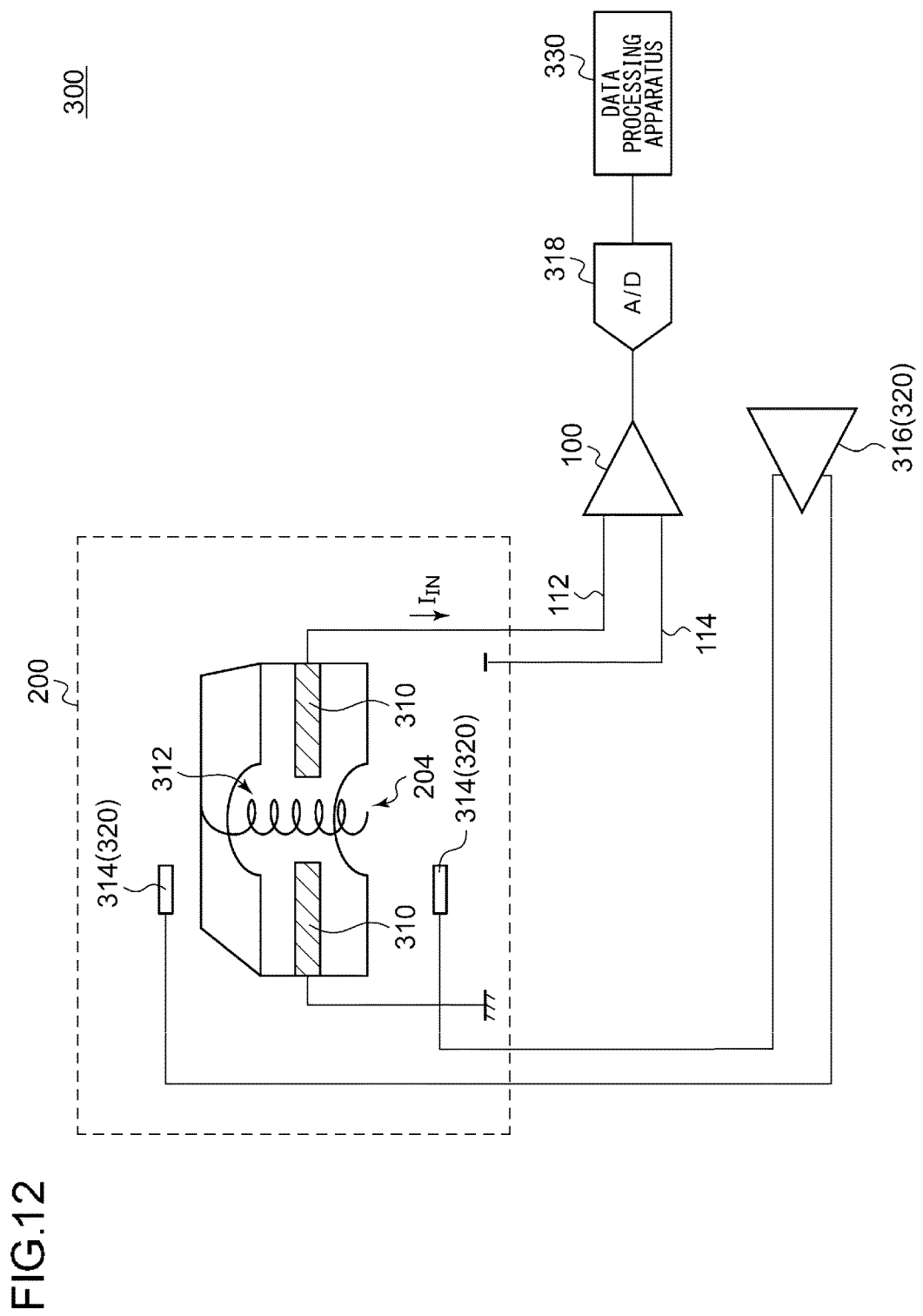
FIG. 12 is a block diagram showing a base sequence analyzing apparatus including a current measurement circuit.

Lastly, description will be made regarding the usage of the current measurement circuit 100. The current measurement circuit 100 according to the embodiment may be employed in a base sequence analyzing apparatus (DNA sequencer or RNA sequencer) 300. FIG. 12 is a block diagram showing the base sequence analyzing apparatus 300 including the current measurement circuit 100. The base sequence analyzing apparatus 300 includes an electrode pair 310, a position control apparatus 320, the aforementioned current measurement circuit 100, and a data processing apparatus 330.

The DUT 200 is configured as a chip including the electrode pair 310, a nanopore structure 312, an electrophoresis electrode pair 314, an unshown nanochannel, an unshown nanopillar structure, and the like. A DNA sample is controlled such that it passes through the nanochannel, so as to separate and extract a single DNA molecule. After the DNA molecule passes through the nanopillar structure, the DNA molecule can be analyzed as a linear sample.

The electrophoresis electrode pair 314 and a driving amplifier 316 form the position control apparatus 320 that controls the position of the DNA molecule 204. The position control apparatus 320 applies an electric field to the DNA molecule so as to move the DNA molecule such that it passes through a gap between the electrode pair 310 formed in the nanopore structure 312.

When a base of the DNA molecule passes through the gap between the electrode pair 310, the tunnel current $I_{IN}$ flows according to the base type. The current measurement circuit 100 detects the tunnel current (current signal) $I_{IN}$, and converts the current signal thus detected into the voltage signal $V_{OUT}$. The voltage signal $V_{OUT}$ is converted by an A/D converter 318 into a digital value. The digital value thus converted is input to the data processing apparatus 330. The data processing apparatus 330 is configured as a computer including memory and a processor. The data processing apparatus 330 performs signal processing so as to identify the base sequence of the DNA molecule.

As described above, the current measurement circuit 100 according to the embodiment provides low-noise characteristics and high-speed operation. Thus, such an arrangement allows the number of times each base is sampled to be increased, thereby providing improved measurement precision. Alternatively, such an arrangement allows the number of bases that can be analyzed per unit time to be increased. Also, such an arrangement is capable of reducing noise that occurs in the current measurement circuit 100. Thus, such an arrangement allows the required number of times each base is sampled to be reduced.

Description has been made with reference to FIG. 12 regarding a sequencer using the gating nanopore method. Also, the current measurement circuit 100 may be applied to a sequencer using the MCBJ method.

While the preferred embodiments of the present invention have been described using specific terms, such description is for illustrative purposes only, and it is to be understood that changes and variations may be made without departing from the spirit or scope of the appended claims.

What is claimed is:

1. A current measurement circuit that converts a current signal into a voltage signal, the current measurement circuit comprising:
   a signal line via which the current signal is transmitted;
   a shield line arranged in the vicinity of at least a part of the signal line;
   a non-inverting amplifier comprising an operational amplifier having its non-inverting input terminal supplied with the current signal the signal line and its inverting input terminal supplied with its output signal as a feedback signal;
   an inverting amplifier that amplifies the output signal of the non-inverting amplifier with inversion so as to generate the voltage signal;
   an impedance circuit comprising a feedback resistor arranged between an output terminal of the inverting amplifier and the non-inverting input terminal of the operational amplifier; and
   a guard amplifier that receives an electric potential at the inverting input terminal of the operational amplifier, and that applies the electric potential to the shield line.

2. The current measurement circuit according to claim 1, further comprising a correction amplifier that corrects frequency characteristics of an output signal of the inverting amplifier.

3. The current measurement circuit according to claim 1, further comprising a shield that covers at least a part of the feedback resistor,
   wherein an output of the guard amplifier is connected to the shield.

4. The current measurement circuit according to claim 3, wherein the shield covers one electrode, which is arranged on an input terminal side of the non-inverting amplifier, of the feedback resistor having two electrodes.

5. The current measurement circuit according to claim 1, further comprising a protection element arranged between the signal line and the shield line.

6. The current measurement circuit according to claim 1, wherein the signal line and the shield line are configured as a cable having a hollow coaxial cable structure or otherwise a low-capacitance coaxial cable structure.

7. The current measurement circuit according to claim 1, wherein the current measurement circuit is integrated on a semiconductor substrate together with a part of a device under test that generates the current signal, and wherein the signal line and the shield line are formed on the semiconductor substrate.

8. The current measurement circuit according to claim 1, wherein the impedance circuit further comprises a feedback capacitor arranged in parallel with the feedback resistor between an output terminal of the inverting amplifier and the non-inverting input terminal of the non-inverting amplifier.

9. A base sequence analyzing apparatus comprising:

an electrode pair;

a position control apparatus that controls a base sequence having a linear structure such that it passes through the electrode pair;

the current measurement circuit according to claim 1, that detects a current that flows between a gap of the electrode pair; and a data processing apparatus that analyzes an output of the current measurement circuit.

* * * * *